(12) United States Patent
Levy et al.

(10) Patent No.: US 10,154,980 B2
(45) Date of Patent: *Dec. 18, 2018

(54) ANTI-INFLAMMATORY OMEGA-3 SYNERGISTIC COMBINATIONS

(71) Applicant: LYCORED LTD., Beer Sheva (IL)

(72) Inventors: Rachel Levy, Omer (IL); Nurit Hadad, Beer Sheva (IL); Tanya Sedlov, Beer Sheva (IL); Morris Zelkha, Ramat Gan (IL); Masha Sapojnik, Beer Sheva (IL)

(73) Assignee: LYCORED LTD., Beer Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/830,402

(22) Filed: Dec. 4, 2017

(65) Prior Publication Data
US 2018/0153843 A1 Jun. 7, 2018

Related U.S. Application Data

(63) Continuation of application No. 14/782,583, filed as application No. PCT/IL2014/050329 on Mar. 4, 2014, now Pat. No. 9,901,562.
(Continued)

(51) Int. Cl.
*A61K 31/202* (2006.01)
*A61K 9/00* (2006.01)
(Continued)

(52) U.S. Cl.
CPC .......... *A61K 31/202* (2013.01); *A61K 9/0053* (2013.01); *A61K 31/01* (2013.01);
(Continued)

(58) Field of Classification Search
None
See application file for complete search history.

(56) References Cited

U.S. PATENT DOCUMENTS 9,468,609 B2   10/2016  Levy et al.
9,901,562 B2 *  2/2018  Levy .................... A61K 31/355
(Continued)

FOREIGN PATENT DOCUMENTS

CN    102355894 A    2/2012
JP    2000060417 A   2/2000
(Continued)

OTHER PUBLICATIONS

Database CAPLUS (2009:1310970) as displayed by CAS SciFinder of KR 2009/109793 A (Oct. 21, 2009) (abstract).*
(Continued)

*Primary Examiner* — Brian J Davis
(74) *Attorney, Agent, or Firm* — The Roy Gross Law Firm, LLC; Roy Gross

(57) ABSTRACT

This invention is directed to compositions having synergistic combinations of omega-3 fatty acid such as OMEGA-3 with a tomato extract lycopene, and optionally with carnosic acid and/or lutein. More specifically, the present invention provides compositions having synergistic combinations of the aforementioned compounds, which may be used, inter alia, to inhibit/suppress inflammation via the suppression of the expression of anti-inflammatory mediators or via the suppression of the secretion of anti-inflammatory mediators from macrophages at a site of inflammation.

6 Claims, 10 Drawing Sheets

Related U.S. Application Data

(60) Provisional application No. 61/808,246, filed on Apr. 4, 2013.

(51) Int. Cl.

| | | |
|---|---|---|
| *A61K 31/01* | (2006.01) | |
| *A61K 31/047* | (2006.01) | |
| *A61K 31/355* | (2006.01) | |
| *A61K 36/81* | (2006.01) | |
| *A61K 31/035* | (2006.01) | |
| *A61K 31/192* | (2006.01) | |

(52) U.S. Cl.
CPC .......... *A61K 31/035* (2013.01); *A61K 31/047* (2013.01); *A61K 31/192* (2013.01); *A61K 31/355* (2013.01); *A61K 36/81* (2013.01); *Y02A 50/411* (2018.01)

(56) References Cited

U.S. PATENT DOCUMENTS

| | | | |
|---|---|---|---|
| 2002/0146400 A1* | 10/2002 | Cincotta | A23L 2/52 424/94.1 |
| 2009/0326056 A1 | 12/2009 | Goralczyk | |

FOREIGN PATENT DOCUMENTS

| | | | | |
|---|---|---|---|---|
| JP | 2013510095 A | | 3/2013 | |
| KR | 2009/109793 A | * | 10/2009 | ............... A23L 1/29 |
| WO | 03068202 A1 | | 8/2003 | |
| WO | 2011057183 A1 | | 5/2011 | |

OTHER PUBLICATIONS

Feng-Yao Tang et al: "Concomitant consumption of lycopene and fish oil inhibits tumor growth and progression in a mouse xenograft model of colon cancer"; Molecular Nutrition & Food Research; vol. 56, No. 10; Sep. 7, 2012; pp. 1520-1531.

Verschuren L et al: "A Dietary Mixture Containing Fish Oil, Resveratrol, Lycopene, Catechins, and Vitamins E and C Reduces Atherosclerosis in Transgenic Mice"; The Journal of Nutrition; vol. 141, No. 5; Mar. 16, 2011; pp. 863-869.

Garcia-Alonso F J et al: "Effect of consumption of tomato juice enriched with n-3 polyunsaturated fatty acids on the lipid profile, antioxidant biomarker status, and cardiovascular disease risk in healthy women"; European Journal of Nutrition; vol. 51, No. 4; Jul. 14, 2011; pp. 415-424.

Yasuno Fumihiko et al: "Combination of Antioxidant Supplements Improved Cognitive Function in the Elderly"; Journal of Alzheimer's Disease; vol. 32, No. 4; Aug. 2012; pp. 895-903.

Nurit Hadad et al: "The synergistic anti-inflammatory effects of lycopene, lutein, [beta]-carotene, and camosic acid combinations via redox-based inhibition of NF-[kappa]B signaling"; Free Radical Biology and Medicine; vol. 53, No. 7; Oct. 2012; pp. 1381-1391.

Palozza P et al: "Tomato Lycopene and Inflammatory Cascade: Basic Interactions and Clinical Implications"; Current Medicinal Chemistry: The New International Journal for Timely In-Depth Reviews in Medicinal Chemistry; vol. 17, No. 23; Aug. 2010; pp. 2547-2563.

Rafi et al: "Dietary lutein modulates inducible nitric oxide synthase (iNOS) gene and protein expression in mouse macrophage cells (RAW 264.7)" Molecular Nutrition & Food Research, vol. 51, Issue 3, pp. 333-340, Mar. 2007.

Rafi et al: "Lycopene inhibits LPS induced pro-inflammatory mediators inducible nitric oxide synthase in mouse macrophage cells"; Journal of Food Science, vol. 72, pp. 69-74, 2007.

Choi et al: "Inhibitions of nNOS and COX-2 expression by lutein in acute retinal ischemia"; Nutrition vol. 22, pp. 668-671, 2006.

Ohata et al., Suppression of Nitric Oxide Production in Lipopolysaccharide-stimulated Macrophage Cells by w3 Polyunsaturated Fatty Acids, Jpn J. Cancer Res., Mar. 1997, 234-237, vol. 88, No. 3.

International Preliminary Report on Patentability of PCT/IL2014/050329 Report dated Oct. 6, 2015 3 pages.

International Search Report of PCT/IL2014/050329 Completed Jul. 21, 2014; dated Jul. 22, 2014 8 pages.

Written Opinion of the International Searching Authority of PCT/IL2014/050329 dated Jul. 22, 2014 7 pages.

Rakuten, Oil sardine recipe / how to make it with round dried sardines, [retrieved on Dec. 13, 2017]. Retrieved from the Internet <URL: https://recipe.rakuten.co.jp/recipe/1860005068>.

* cited by examiner

ANTI-INFLAMMATORY OMEGA-3 SYNERGISTIC COMBINATIONS

FIELD OF INVENTION

This invention is directed to, inter alia, a composition comprising a synergistic combination of an omega-3 fatty acid with lycopene. More specifically, the present invention provides a composition comprising a synergistic combination of the aforementioned compounds, which may be used, inter alia, to inhibit/suppress inflammation.

BACKGROUND OF THE INVENTION

The inflammatory process, which forms an important part of the non-specific immune system, is characterized by a complex set of chemical and cellular changes that are essential for host defense in the face of microbial agents and other potentially harmful environmental factors. However, in many cases, inflammation may be triggered inappropriately, and/or may persist to a degree which becomes harmful to the host. In such cases, there may be a need to inhibit or prevent the development of one or more aspects of the inflammatory process, in particular, in cases of non-infectious inflammatory diseases.

A very large number of different chemical mediators have been shown to be involved in the development and control of the inflammatory process. Recent studies by a number of different laboratories have implicated nitric oxide (NO) as an important modulator of a variety of acute and chronic inflammatory disorders, including various types of arthritis, gastro-intestinal diseases, inflammatory conditions of the central nervous system and certain forms of asthma. Consequently, it has been proposed that inhibition of NO production could provide a useful therapeutic mechanism for the treatment and/or management of these inflammatory disorders. Furthermore, inhibition of NO synthesis has also been shown to be useful in some conditions or states that are not primarily inflammatory in nature. Thus, for example, inhibition of NO synthesis has been found to reduce glucose uptake into limb tissue in individuals with Type 2 diabetes during exercise.

The in vivo production of NO is mediated by a family of nitric oxide synthase (NOS) enzymes, including inducible-nitric oxide synthase (I-NOS), which is activated by many different immunological stimuli including lipopolysaccharide (LPS), interferon gamma and interleukin 1 (IL-1).

In addition, several other compounds, including a number of natural products, have also been shown to inhibit NO production. The latter group includes compounds such as lutein [Rafi M. M. et al. Mol Nutr Food Res. 2007 March; 51(3):333-40; Choi, J. S. Nutrition. 2006 June; 22(6):668-71] and lycopene [Rafi, M. M. et al. J Food Sci. 2007 January; 72(1): S069-74]. However, the efficacy and potency of many of the natural product NO inhibitors have proven to be not particularly high. A need therefore exists for improved NO production-inhibiting compositions of natural origin.

It is a purpose of the present invention to provide a composition that may be used to inhibit the production of one or more key inflammatory mediators, such as superoxide NO or TNF-alpha, as a means for treating or managing pathological states and processes in which said mediators are implicated.

It is another purpose of the invention to provide a composition that is able to inhibit the production of the aforesaid inflammatory mediators with greater efficacy and/or potency than the compounds and compositions reported in the prior art.

SUMMARY OF THE INVENTION

In one embodiment, the present invention provides a composition comprising tomato lycopene or Lyc-O-Mato®, an omega-3 fatty acid, and carnosic acid. In another embodiment, the present invention further provides a composition comprising tomato lycopene or Lyc-O-Mato®, an omega-3 fatty acid, lutein and carnosic acid. In another embodiment, the present invention further provides that the composition further comprises lutein, phytoene, phytofluene, beta-carotene, a tocopherol, phytosterols, or any combination thereof. In another embodiment, the present invention further provides that the molar concentration ratio of an omega-3 fatty acid to tomato lycopene is from 2000:1 to 10:1. In another embodiment, the present invention further provides that the molar concentration ratio of omega-3 fatty acid to carnosic acid is from 1500:1 to 2:1. In another embodiment, the present invention further provides that the molar concentration ratio of omega-3 fatty acid to tomato lycopene to carnosic acid is from 2000:1:5 to 2:1:1. In another embodiment, the present invention further provides that an omega-3 fatty acid is ROPUFA®. In another embodiment, the present invention further provides that an omega-3 fatty acid is docosahexaenoic acid, eicosapentaenoic acid, or a combination thereof. In another embodiment, the present invention further provides that the composition has a synergistic anti-inflammatory effect.

In another embodiment, the present invention further provides a method for treating a subject afflicted with inflammation, comprising the step of administering to the subject a therapeutically effective amount of a composition comprising: (1) an omega-3 fatty acid and (2) tomato lycopene, thereby treating a subject afflicted with inflammation. In another embodiment, the present invention further provides that treating a subject afflicted with inflammation is inhibiting the production of NO, PGE2, TNF-alpha, or any combination thereof.

| Sample | EPA | DHA |
|---|---|---|
| 1 | 3170 | 1540 |
| 2 | 1585 | 770 |
| 3 | 792.5 | 385 |
| 4 | 630 | 308 |
| 5 | 315 | 154 |
| 6 | 157.5 | 77 |
| 7 | 78.75 | 38.5 |
| 8 | 39.375 | 19.25 |
| 9 | 19.6875 | 9.625 |

Figure 1A:
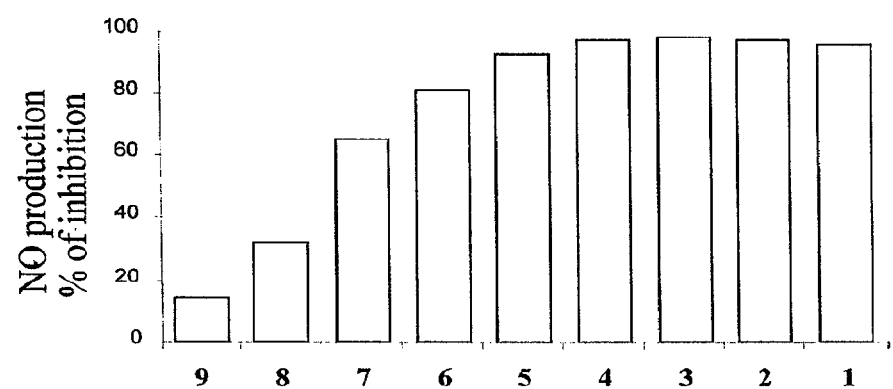
FIGS. 1A-1B. Bar graphs (FIG. 1A and FIG. 1B) showing dose dependent inhibition of NO production in cells by OMEGA-3. (EPA and DHA concentrations (in micromolar) in FIG. 1A are as follows.
Figure 1B:
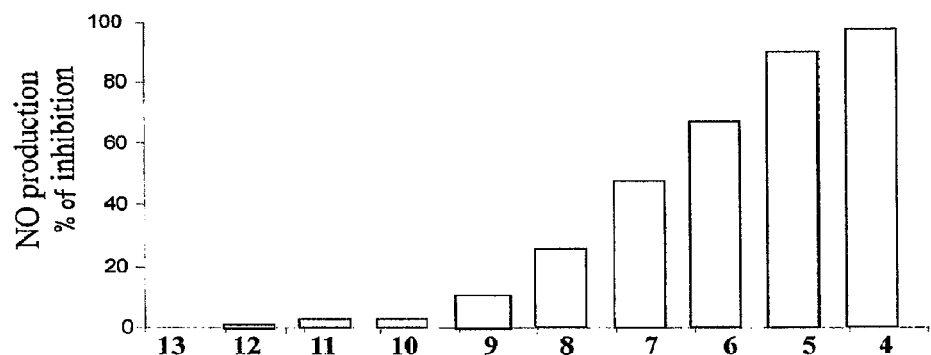
Figure 2A:
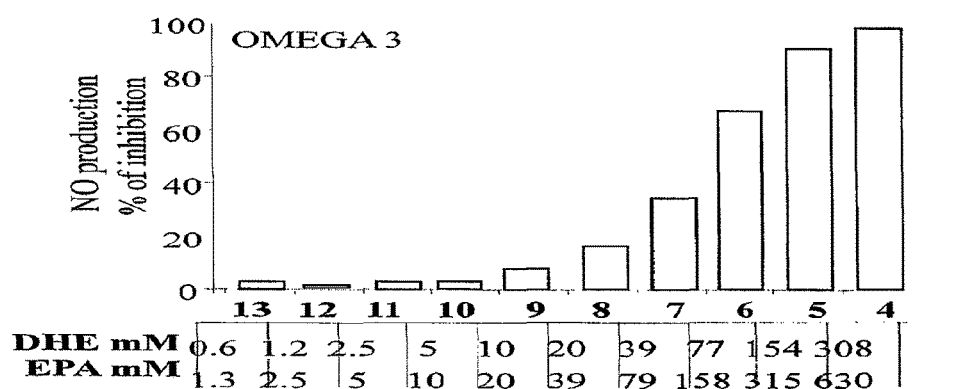
Figure 2B:
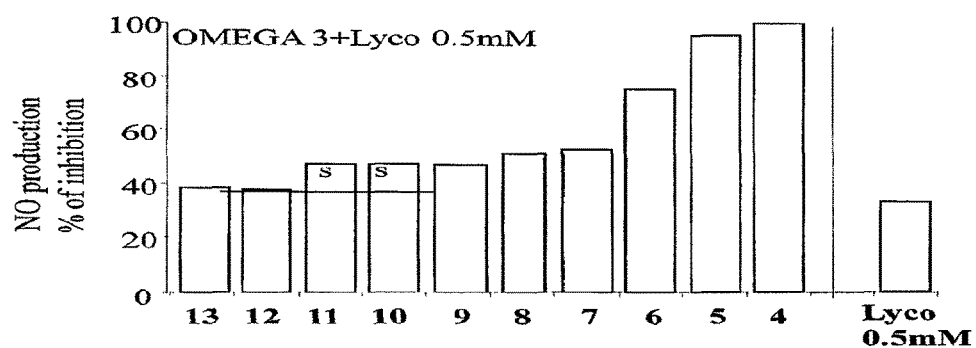
Figure 2C:
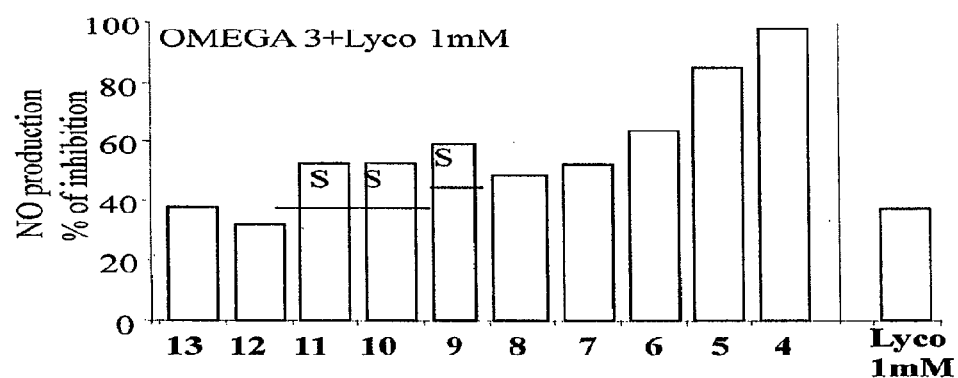
Figure 2D:
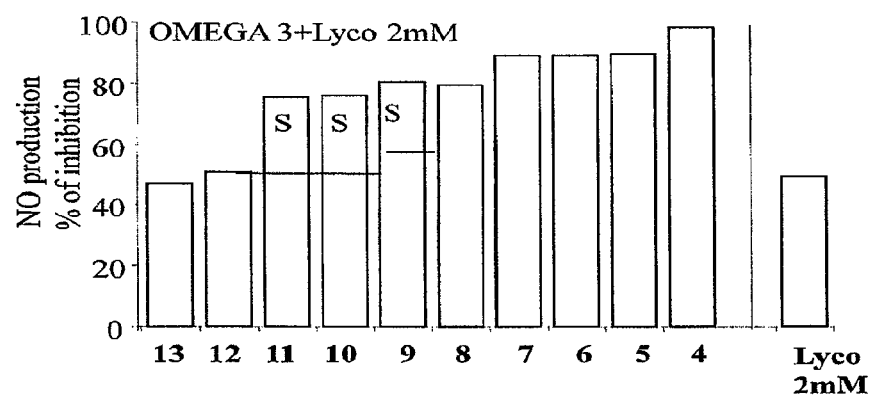

EPA and DHA concentrations (in micromolar) in FIG. 1B are as follows:

| Sample | EPA | DHA |
|---|---|---|
| 4 | 630 | 308 |
| 5 | 315 | 154 |

-continued

| Sample | EPA | DHA |
|---|---|---|
| 6 | 157.5 | 77 |
| 7 | 78.75 | 38.5 |
| 8 | 39.38 | 19.25 |
| 9 | 19.69 | 9.62 |
| 10 | 9.84 | 4.81 |
| 11 | 4.92 | 2.40 |
| 12 | 2.46 | 1.20 |
| 13 | 1.23 | 0.60 |

FIGS. 2A-2D. Are bar graphs showing the dose dependent synergistic inhibition effect of NO production in cells by OMEGA-3 (FIG. 2A) and the combinations of various concentrations of Lyc-O-Mato® and OMEGA-3 (0.5 micromolar Lyc-O-Mato® (FIG. 2B), 1 micromolar Lyc-O-Mato® (FIG. 2C), and 2 micromolar Lyc-O-Mato® (FIG. 2D)). Omega-3 EPA and DHA concentrations (in micromolar) correspond to the same samples as FIG. 1 Bars marked with "S" exhibited a synergistic effect which is the upper portion of the bar.

Figure 3A:
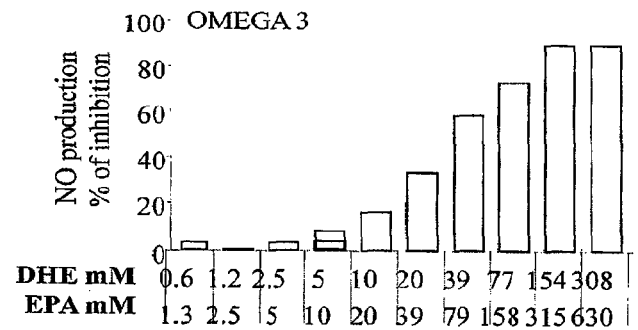
Figure 3B:
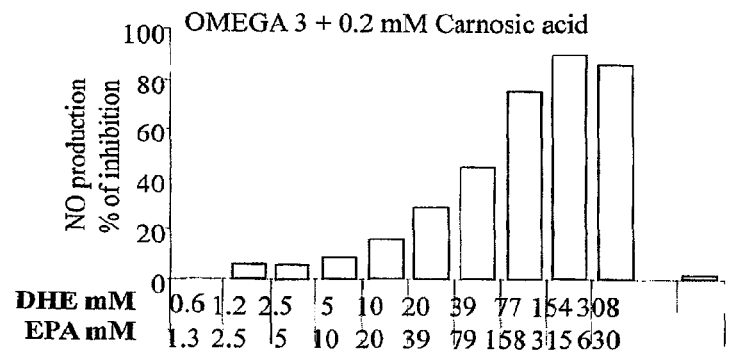
Figure 3C:
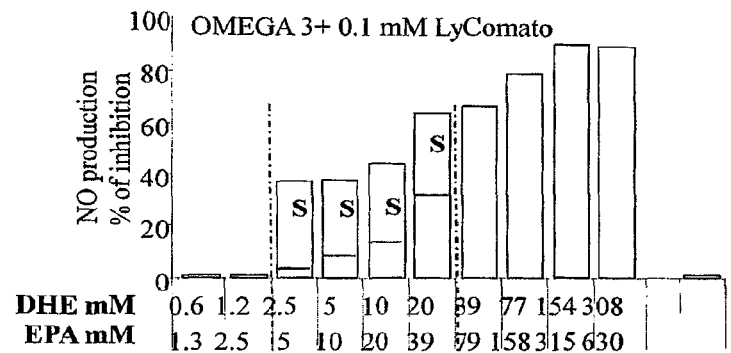
Figure 3D:
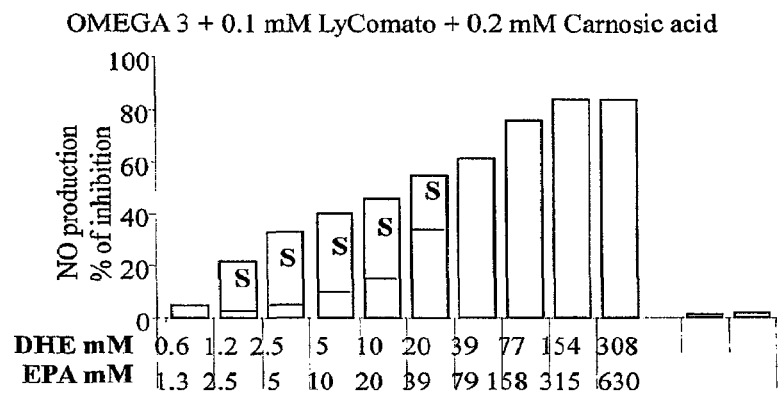

FIGS. 3A-3D. Bar graphs showing the dose dependent synergistic inhibition effect of NO production in cells by OMEGA-3, carnosic acid, and Lyc-O-Mato®. FIG. 3A is Omega-3, FIG. 3B is Omega-3 and 0.2 micromolar Carsonic acid, FIG. 3C is Omega-3 and 0.1 micromolar Lyc-O-Mato®, and FIG. 3D is Omega-3 and 0.2 micromolar Carsonic acid and 0.1 micromolar Lyc-O-Mato®.

Figure 4A:
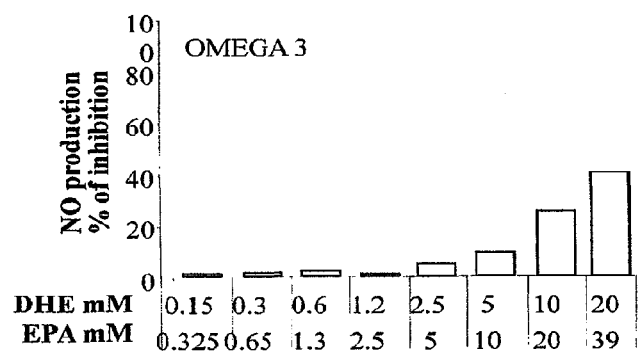
Figure 4B:
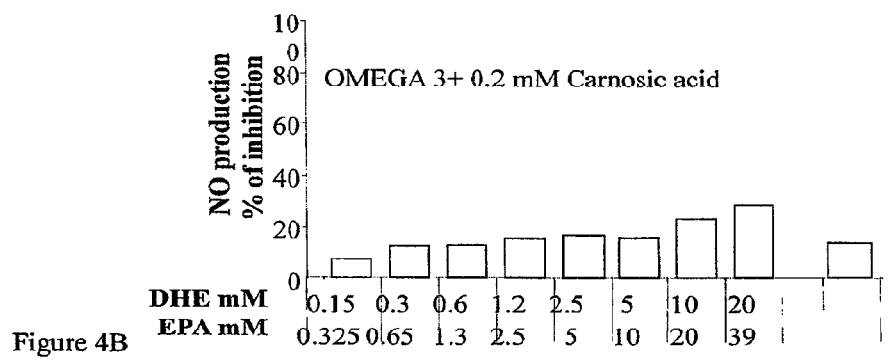
Figure 4C:
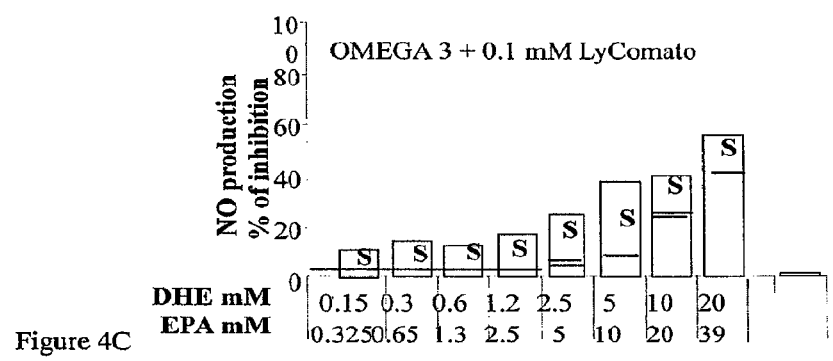
Figure 4D:
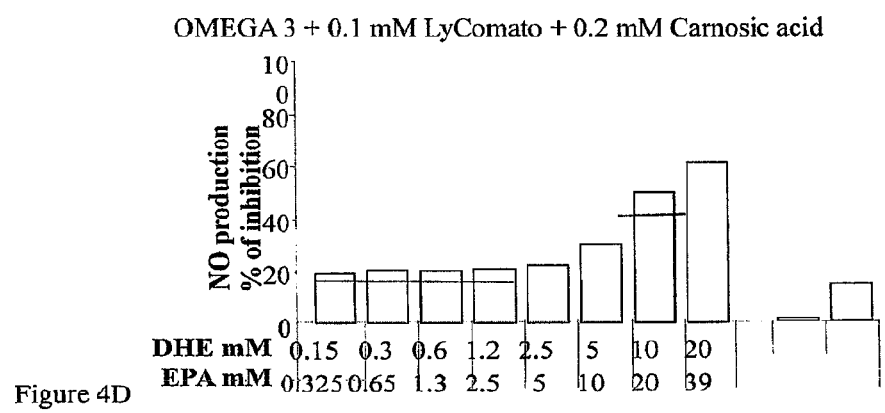

FIGS. 4A-4D. Bar graphs showing the dose dependent synergistic inhibition effect of NO production by OMEGA-3, carnosic acid, and Lyc-O-Mato®. FIG. 3A/FIG. 4A is Omega-3, FIG. 3B/FIG. 4B is Omega-3 and 0.2 micromolar Carsonic acid, FIG. 3C/FIG. 4C is Omega-3 and 0.1 micromolar Lyc-O-Mato®, and FIG. 3D/FIG. 4D is Omega-3 and 0.2 micromolar Carsonic acid and 0.1 micromolar Lyc-O-Mato®. Bars marked with "S" exhibited a synergistic effect which is the upper portion of the bar.

Figure 5A:
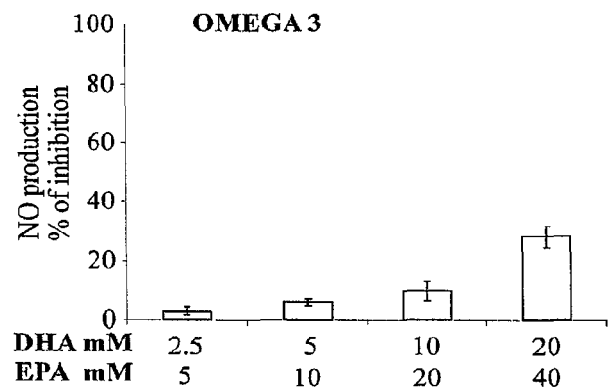
Figure 5B:
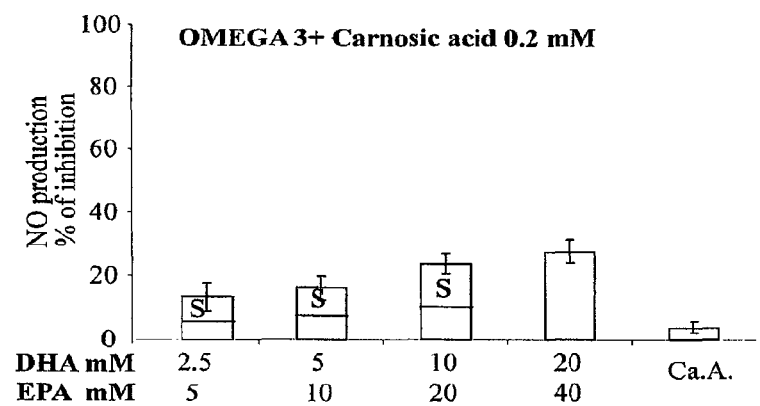
Figure 5C:
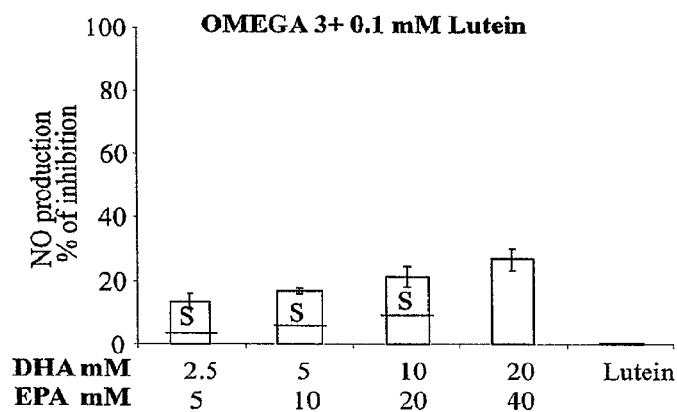
Figure 5D:
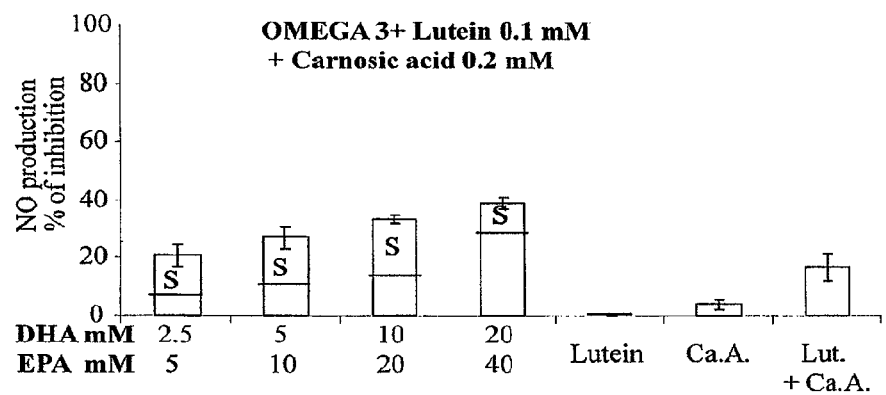

FIGS. 5A-5D. Bar graphs showing the dose dependent synergistic inhibition of NO production in cells by OMEGA-3, carnosic acid, and lutein. FIG. 5A is Omega-3, FIG. 5B is Omega-3 and 0.2 micromolar Carsonic acid, FIG. 5C is Omega-3 and 0.1 micromolar Lutein, and FIG. 5D is Omega-3 and 0.2 micromolar Carsonic acid and 0.1 micromolar Lutein. Bars marked with "S" exhibited a synergistic effect which is the upper portion of the bar.

Figure 6A:
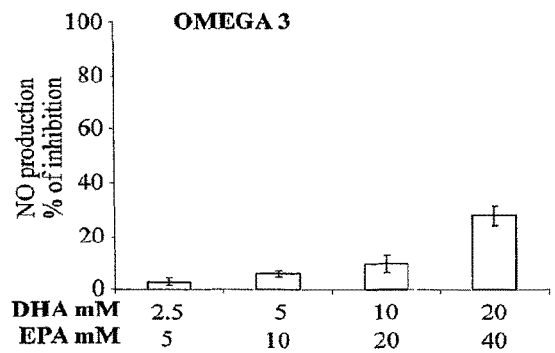
Figure 6B:
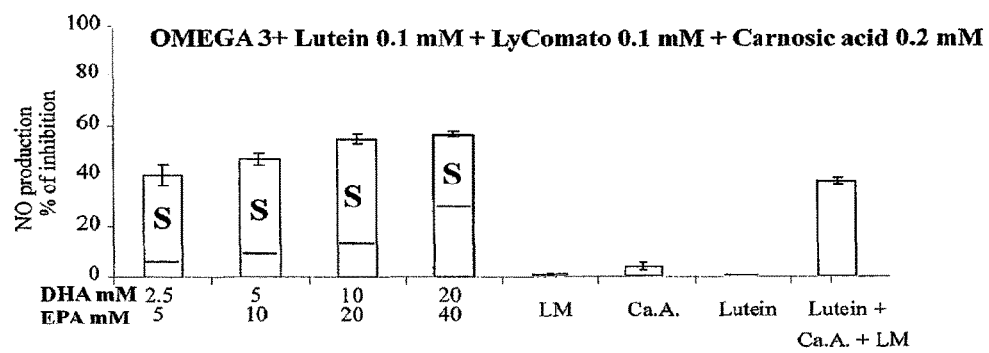

FIGS. 6A-6B. Bar graphs showing that omega-3 fatty acids DHA and EPA with carnosic acid, lutein and tomato lycopene, synergistically inhibited NO production in cells. FIG. 6A is Omega-3 and FIG. 6B is Omega-3 and 0.2 micromolar Carsonic acid and 0.1 micromolar Lutein and 0.1 micromolar Lyc-O-Mato®. Bars marked with "S" exhibited a synergistic effect which is the upper portion of the bar.

Figure 7A:
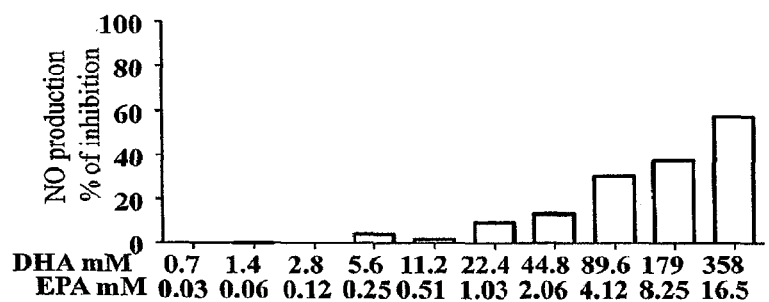
Figure 7B:
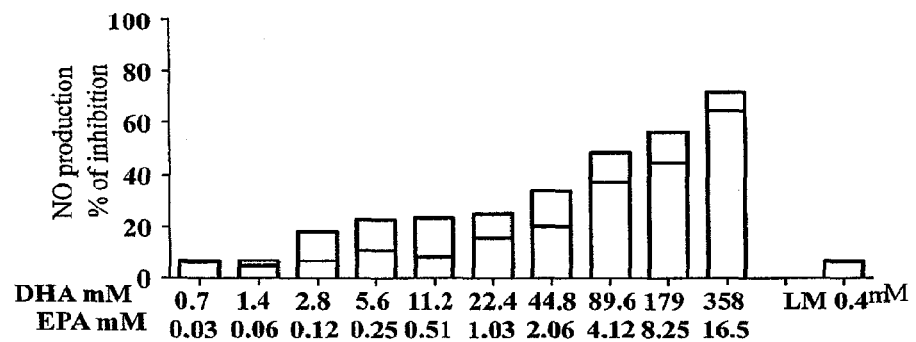

FIGS. 7A-7B. Bar graphs showing that omega-3 oil with higher DHA content than EPA is also effective in the inhibition of NO production in cells (FIG. 7A). A combination of omega-3 with higher DHA content than EPA and tomato lycopene is provided in FIG. 7B, the upper portion of bars, which are divided to 2, is the synergistic portion of the inhibition of NO in cells, obtained by both Omega-3 and tomato lycopene.

DETAILED DESCRIPTION OF THE INVENTION

In one embodiment, the present invention provides a composition comprising an omega-3 fatty acid and tomato lycopene. In one embodiment, the present invention provides a composition comprising a synergistic (as further explained hereinbelow) combination of omega-3 fatty acid and tomato lycopene. In one embodiment, the present invention provides a composition comprising an omega-3 fatty acid, carnosic acid, and tomato lycopene. In one embodiment, the present invention provides a composition comprising a synergistic (as further explained hereinbelow) combination of an omega-3 fatty acid, carnosic acid, and tomato lycopene. In one embodiment, the present invention provides a composition comprising an omega-3 fatty acid, lutein, and tomato lycopene. In one embodiment, the present invention provides a composition comprising an omega-3 fatty acid, lutein, carnosic acid, and tomato lycopene. In one embodiment, the present invention provides a composition comprising a synergistic (as further explained hereinbelow) combination of an omega-3 fatty acid, lutein, carnosic acid, and tomato lycopene.

According to some embodiments, tomato lycopene is far more effective than synthetic lycopene in its anti-inflammation activity as measured by inhibition of NO production.

In another embodiment, tomato lycopene is lycopene extracted from a tomato plant. In another embodiment, tomato lycopene is a tomato extract enriched for lycopene. In another embodiment, tomato lycopene is a lycopene-rich tomato extract which is all-natural. In another embodiment, tomato lycopene is a tomato lycopene complex. In another embodiment, tomato lycopene complex comprises a complex of phytonutrients including phytoene, phytofluene, beta-carotene, tocopherols and phytosterols. In another embodiment, tomato lycopene is Lyc-O-Mato® (LycoRed Ltd., Be'er Sheva, Israel). In another embodiment, a composition of the invention comprises tomato lycopene and an omega-3 fatty acid. In another embodiment, a composition of the invention comprises Lyc-O-Mato® and an omega-3 fatty acid.

Suitable processes for preparing this extract and similar extracts are described in U.S. Pat. No. 5,837,311, the specification of which is incorporated herein by reference in its entirety. However, it is to be recognized that many other types of preparatory procedures may be used to obtain the composition from a variety of plant sources.

In another embodiment, an omega-3 fatty acid is in oil. In another embodiment, an omega-3 fatty acid is derived from marine or plant oils. In another embodiment, an omega-3 fatty acid is derived from fish oil. In another embodiment, an omega-3 fatty acid is derived from algal oil. In another embodiment, an omega-3 fatty acid is derived from squid oil. In another embodiment, an omega-3 fatty acid is derived from Echium oil. In another embodiment, an omega-3 fatty acid is derived from flaxseed oil. In another embodiment, an omega-3 fatty acid is fish oil. In another embodiment, an omega-3 fatty acid is algal oil. In another embodiment, an omega-3 fatty acid is squid oil. In another embodiment, an omega-3 fatty acid is oil.

In another embodiment, an omega-3 fatty acid comprises high DHA and low EPA (see experimental section and figures). In another embodiment, an omega-3 fatty acid comprises low DHA and high EPA (see experimental section and figures). In another embodiment, an omega-3 fatty acid is eicosapentaenoic acid (EPA). In another embodiment, an omega-3 fatty acid is docosahexaenoic acid (DHA). In another embodiment, an omega-3 fatty acid is alpha-linolenic acid (ALA). In another embodiment, an omega-3 fatty acid is a combination of EPA and DHA. In another embodiment, an omega-3 fatty acid is a combination of EPA, DHA, and ALA. In another embodiment, an omega-3 fatty acid is a combination of EPA and ALA. In another embodiment, an omega-3 fatty acid is a combination of DHA and ALA. In another embodiment, the omega-3 fatty acid is ROPUFA®.

In another embodiment, a composition as described herein comprises both EPA and DHA in a molar ratio of 1:5 to 1:1. In another embodiment, a composition as described herein comprises both EPA and DHA in a molar ratio of 1:10 to 2:1. In another embodiment, a composition as described herein comprises both EPA and DHA in a molar ratio of 1:8 to 1:2. In another embodiment, a composition as described herein comprises both EPA and DHA in a molar ratio of 1:4 to 1:1.5.

In another embodiment, a composition as described herein comprises both EPA and DHA in a molar ratio of 5:1 to 1:1. In another embodiment, a composition as described herein comprises both EPA and DHA in a molar ratio of 10:1 to 2:1. In another embodiment, a composition as described herein comprises both EPA and DHA in a molar ratio of 4:1 to 1:3. In another embodiment, a composition as described herein comprises both EPA and DHA in a molar ratio of 2.5:1 to 1:2.5.

In another embodiment, a composition as described herein further comprises phytoene. In another embodiment, a composition as described herein further comprises phytofluene. In another embodiment, a composition as described herein further comprises beta-carotene. In another embodiment, a composition as described herein further comprises tocopherol. In another embodiment, a composition as described herein further comprises phytosterols. In another embodiment, a composition as described herein further comprises a combination of any two or more of: phytoene, phytofluene, beta-carotene, tocopherol, and phytosterols. In another embodiment, phytoene, phytofluene, beta-carotene, tocopherol, and phytosterols are of natural source. In another embodiment, phytoene, phytofluene, beta-carotene, tocopherol, and phytosterols are derived from tomato. In another embodiment, phytoene, phytofluene, beta-carotene, tocopherol, phytosterols, or any combination thereof is produced synthetically.

In another embodiment, the molar concentration ratio of an omega-3 fatty to tomato lycopene is from 4000:1 to 1:1. In another embodiment, the molar concentration ratio of an omega-3 fatty acid to tomato lycopene is from 1000:1 to 10:1. In another embodiment, the molar concentration ratio of an omega-3 fatty acid to tomato lycopene is from 500:1 to 50:1. In another embodiment, the molar concentration ratio of an omega-3 fatty acid to tomato lycopene is from 200:1 to 1:1. In another embodiment, the molar concentration ratio of an omega-3 fatty acid to tomato lycopene is from 150:1 to 20:2.

In another embodiment, the molar concentration ratio of tomato lycopene to EPA to DHA is from 1:200:400 to 1:600:600. In another embodiment, the molar concentration ratio of tomato lycopene to EPA to DHA is from 1:100:100 to 1:300:100. In another embodiment, the molar concentration ratio of tomato lycopene to EPA to DHA is from 1:50:100 to 1:150:250.

In another embodiment, the molar concentration ratio of lutein to tomato lycopene to carnosic acid to EPA to DHA is from 1:200:400 to 1:600:600. In another embodiment, the molar concentration ratio of tomato lycopene to EPA to DHA is from 1:1:2:200:400 to 1:1:4:400:400. In another embodiment, the molar concentration ratio of tomato lycopene to EPA to DHA is from 1:1:1:500:500 to 2:1:4:100:100. In another embodiment, the molar concentration ratio of tomato lycopene to EPA to DHA is from 1:1:1:100:500 to 1:1:1:200:200.

In another embodiment, the molar concentration ratio of an omega-3 fatty to carnosic acid in a composition of the invention is from 3500:1 to 1:1. In another embodiment, the molar concentration ratio of an omega-3 fatty acid to carnosic acid in a composition of the invention is from 2000:1 to 1:1. In another embodiment, the molar concentration ratio of an omega-3 fatty acid to carnosic acid in a composition of the invention is from 1500:1 to 50:1. In another embodiment, the molar concentration ratio of an omega-3 fatty acid to carnosic acid in a composition of the invention is from 500:1 to 100:1.

In another embodiment, the molar concentration ratio of an omega-3 fatty to tomato lycopene to carnosic acid in a composition of the invention is from 5000:1:2 to 50:1:1. In another embodiment, the molar concentration ratio of an omega-3 fatty acid to tomato lycopene to carnosic acid in a composition of the invention is from 2500:1:5 to 20:1:2. In another embodiment, the molar concentration ratio of an omega-3 fatty acid to tomato lycopene to carnosic acid in a composition of the invention is from 1000:1:10 to 100:1:10. In another embodiment, the molar concentration ratio of an omega-3 fatty acid to tomato lycopene to carnosic acid in a composition of the invention is from 2000:1:2 to 50:1:1.

In another embodiment, the molar concentration ratio of lutein to lycopene to carnosic acid is 1:1:1 to 1:2:4. In another embodiment, the molar concentration ratio of lutein to lycopene to carnosic acid is 1:1:1 to 1:2:4.

In another embodiment, a composition of the invention further comprises lutein. In another embodiment, lutein comprises (3R,3'R, 6'R)-beta,epsilon-carotene-3,3'-diol. In another embodiment, to lutein is a plant lutein. In another embodiment, lutein is Marigold lutein. In another embodiment, lutein is a synthetic lutein. In another embodiment, lutein comprises saponifying fatty acid.

The components of the above-disclosed compositions may be purified compounds, synthetic compounds or may be present in mixture with other components, for example in plant extracts such as rosemary extract (in the case of carnosic acid), marigold extract (in the case of lutein) or a tomato extract (such as Lyc-O-Mato®-which is commercially available from LycoRed, Be'er Sheva, Israel—in the case of lycopene and other carotenoids).

In some embodiments, a composition as described herein has a synergistic anti-inflammatory effect. In some embodiments, a composition as described herein is an oral composition. In some embodiments, a composition as described herein further comprises a pharmaceutical acceptable excipient.

In some embodiments, a composition as described herein inhibits the production and/or secretion of inflammatory mediators and cytokines which play roles in the pathogenesis of a vast number of mammal inflammatory diseases. In another embodiment, a composition of the invention is a phytonutrient combination causing an immediate, efficient, and synergistic inhibition of LPS-induced internal superoxide production.

In another embodiment, the present invention further provides a method for treating a subject afflicted with inflammation or septic shock, comprising the step of administering to the subject a therapeutically effective amount of a composition as described herein. In another embodiment, the present invention further provides a method for inhibiting the production of proinflammatory cytokines, such as but not limited to TNF-α by macrophages and monocytes at inflammatory sites comprising the step of administering to a subject in need a therapeutically effective amount of a composition as described herein. In another embodiment, the present invention further provides a method for inhibiting the release of proinflammatory cytokines, such as but not limited to TNF-α by macrophages and monocytes at inflammatory sites comprising the step of administering to a subject in need a therapeutically effective amount of a composition as described herein.

In another embodiment, the present invention further provides a method for treating a subject afflicted with inflammation, wherein the inflammation is an inherent part of a disease state. In another embodiment, the present invention further provides a method for treating rheumatoid arthritis. In another embodiment, the present invention further provides a method for treating Crohn's disease. In another embodiment, the present invention further provides a method for treating ulcerative colitis. In another embodiment, the present invention further provides a method for treating septic shock syndrome. In another embodiment, the present invention further provides a method for treating atherosclerosis. In another embodiment, the present invention further provides a method for treating juvenile rheumatoid arthritis. In another embodiment, the present invention further provides a method for treating psoriatic arthritis. In another embodiment, the present invention further provides a method for treating osteoarthritis. In another embodiment, the present invention further provides a method for treating refractory rheumatoid arthritis. In another embodiment, the present invention further provides a method for treating chronic non-rheumatoid arthritis. In another embodiment, the present invention further provides a method for treating osteoporosis/bone resorption. In another embodiment, the present invention further provides a method for treating endotoxic shock. In another embodiment, the present invention further provides a method for treating ischemia-reperfusion injury. In another embodiment, the present invention further provides a method for treating coronary heart disease. In another embodiment, the present invention further provides a method for treating vasculitis. In another embodiment, the present invention further provides a method for treating amyloidosis. In another embodiment, the present invention further provides a method for treating multiple sclerosis. In another embodiment, the present invention further provides a method for treating sepsis. In another embodiment, the present invention further provides a method for treating chronic recurrent uveitis. In another embodiment, the present invention further provides a method for treating hepatitis C virus infection. In another embodiment, the present invention further provides a method for treating malaria. In another embodiment, the present invention further provides a method for treating ulcerative colitis. In another embodiment, the present invention further provides a method for treating cachexia. In another embodiment, the present invention further provides a method for treating plasmocytoma. In another embodiment, the present invention further provides a method for treating endometriosis. In another embodiment, the present invention further provides a method for treating Behcet's disease. In another embodiment, the present invention further provides a method for treating Wegenrer's granulomatosis. In another embodiment, the present invention further provides a method for treating an autoimmune disease. In another embodiment, the present invention further provides a method for treating ankylosing spondylitis. In another embodiment, the present invention further provides a method for treating common variable immunodeficiency (CVID). In another embodiment, the present invention further provides a method for treating chronic graft-versus-host disease. In another embodiment, the present invention further provides a method for treating trauma and transplant rejection. In another embodiment, the present invention further provides a method for treating adult respiratory distress syndrome. In another embodiment, the present invention further provides a method for treating pulmonary fibrosis. In another embodiment, the present invention further provides a method for treating a lymphoproliferative disease. In another embodiment, the present invention further provides a method for treating refractory multiple myeloma. In another embodiment, the present invention further provides a method for treating myeloproliferative disorder. In another embodiment, the present invention further provides a method for treating diabetes. In another embodiment, the present invention further provides a method for treating juvenile diabetes. In another embodiment, the present invention further provides a method for treating meningitis. In another embodiment, the present invention further provides a method for treating skin delayed type hypersensitivity disorders. In another embodiment, the present invention further provides a method for treating Alzheimer's disease. In another embodiment, the present invention further provides a method for treating systemic lupus erythematosus. In another embodiment, the present invention further provides a method for treating any other clinical condition which is inherently associated or depends on an inflammatory process.

In another embodiment, the present invention provides that treating a subject afflicted with inflammation is inhibiting the production of an anti-inflammatory cytokine, a glucocorticoid, an anti-inflammatory neuropeptide, or a lipid inflammation mediator. In another embodiment, the present invention provides that treating a subject afflicted with inflammation is inhibiting the production of NO, PGE, TNF-alpha, or any combination thereof at a site of inflammation. In another embodiment, the present invention provides that treating a subject afflicted with inflammation is inhibiting the production of NO, PGE, TNF-alpha, or any combination thereof by macrophages. In another embodiment, the present invention provides that treating a subject afflicted with inflammation is inhibiting the recruitment of neutrophils to the site of inflammation. In another embodiment, the present invention provides that treating a subject afflicted with inflammation is inhibiting neutrophils activation at the site of inflammation. In another embodiment, PGE is PGE2 (prostaglandin E2).

Furthermore, the present invention also provides a method of treatment of pathological conditions in which superoxide ions, NO, TNF-alpha and/or PGE2 acts as a modulator or mediator of the condition in a mammalian subject in need of such treatment, wherein the method comprises administering to the subject a therapeutic composition according to any one of the embodiments disclosed hereinabove.

In another aspect, the present invention is directed to the use of a composition such as described herein for the manufacture of a medicament for the treatment of conditions responsive to inhibition of NO, TNF-alpha and/or PGE2 production.

In some embodiments of the methods described hereinabove, the subject is a human subject. In some embodiments of the methods described hereinabove, the subject is a mammal. In some embodiments of the methods described hereinabove, the subject is a pet. In some embodiments of the methods described hereinabove, the subject is a farm animal. In some embodiments of the methods described hereinabove, the subject is a lab animal.

While in the above-disclosed methods, the therapeutic composition may be administered by any convenient means, in one embodiment the composition is administered in a pharmaceutical dosage form. In another preferred embodiment, however, the therapeutic composition is incorporated into a foodstuff or beverage.

In one embodiment, the composition of the present invention can be provided to the individual per-se. In one embodiment, the composition of the present invention can be provided to the individual as part of a further pharmaceutical composition where it is mixed with a pharmaceutically acceptable carrier.

In one embodiment, a "pharmaceutical composition" refers to a preparation of a composition as described herein with other chemical components such as physiologically suitable carriers and excipients. The purpose of a pharmaceutical composition is to facilitate administration of the composition to an organism.

In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered composition. An adjuvant is included under these phrases.

In one embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference in its entirety.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In one embodiment, the preparation is administered in a local rather than systemic manner, for example, via injection of the preparation directly into a specific region of a patient's body.

Various embodiments of dosage ranges are contemplated by this invention. The dosage of the composition of the present invention, in one embodiment, is in the range of 0.5-2000 mg/day. In another embodiment, the dosage is in the range of 5-500 mg/day. In another embodiment, the dosage is in the range of 500-2000 mg/day. In another embodiment, the dosage is in the range of 0.1-10 mg/day. In another embodiment, the dosage is in the range of 50-500 mg/day. In another embodiment, the dosage is in the range of 5-4000 mg/day. In another embodiment, the dosage is in the range of 0.5-50 mg/day. In another embodiment, the dosage is in the range of 5-80 mg/day. In another embodiment, the dosage is in the range of 100-1000 mg/day. In another embodiment, the dosage is in the range of 1000-2000 mg/day. In another embodiment, the dosage is in the range of 200-600 mg/day. In another embodiment, the dosage is in the range of 400-1500 mg/day. In another embodiment, the dosage is in a range of 800-1500 mg/day. In another embodiment, the dosage is in the range of 500-2500 mg/day. In another embodiment, the dosage is in a range of 600-1200 mg/day. In another embodiment, the dosage is in the range of 1200-2400 mg/day. In another embodiment, the dosage is in the range of 40-60 mg/day. In another embodiment, the dosage is in a range of 2400-4000 mg/day. In another embodiment, the dosage is in a range of 450-1500 mg/day. In another embodiment, the dosage is in the range of 1500-2500 mg/day. In another embodiment, the dosage is in the range of 5-10 mg/day. In another embodiment, the dosage is in the range of 550-1500 mg/day.

In one embodiment, the dosage is 200 mg/day. In another embodiment, the dosage is 300 mg/day. In another embodiment, the dosage is 400 mg/day. In another embodiment, the dosage is 500 mg/day. In another embodiment, the dosage is 600 mg/day. In another embodiment, the dosage is 700 mg/day. In another embodiment, the dosage is 800 mg/day. In another embodiment, the dosage is 900 mg/day. In another embodiment, the dosage is 1000 mg/day.

Oral administration, in one embodiment, comprises a unit dosage form comprising tablets, capsules, lozenges, chewable tablets, suspensions, emulsions and the like. Such unit dosage forms comprise a safe and effective amount of the composition. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.012% to about 0.933% of the composition, or in another embodiment, from about 0.033% to about 0.7%.

In some embodiments, pharmaceutical compositions for use in the methods of this invention comprise solutions or emulsions, which in some embodiments are aqueous solutions or emulsions comprising a safe and effective amount of the composition of the present invention and optionally, other compounds, intended for topical intranasal administration. In some embodiments, the compositions comprise from about 0.01% to about 10.0% w/v of a subject composition.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the composition of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions include aqueous solutions of the active preparation in water-soluble form. Additionally, suspensions of the active ingredients, in some embodiments, are prepared as appropriate oily or water based suspensions. Suitable lipophilic solvents or vehicles include, in some embodiments, fatty oils such as sesame oil, or synthetic fatty acid esters such as ethyl oleate, triglycerides or liposomes. Aqueous suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In some embodiments, pharmaceutical compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material, the compositions of the invention, into or onto particulate preparations of polymeric compounds such as polylactic acid, polglycolic acid, hydrogels, etc, or onto liposomes, microemulsions, micelles, unilamellar or multi-lamellar vesicles, erythrocyte ghosts, or spheroplasts.) Such compositions will influence the physical state, solubility, stability, rate of in vivo release, and rate of in vivo clearance. Also comprehended by the invention are particulate compositions coated with polymers (e.g. poloxamers or poloxamines).

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the composition described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also be prepared, placed in an appropriate container, and labeled for treatment of an indicated condition.

In one embodiment, compositions of the present invention are presented in a pack or dispenser device, such as an FDA approved kit, which contain one or more unit dosage forms containing the composition. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include chemical, molecular, biochemical, and cell biology techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); "Cell Biology: A Laboratory Handbook", Volumes I-III Cellis, J. E., ed. (1994); The Organic Chemistry of Biological Pathways by John McMurry and Tadhg Begley (Roberts and Company, 2005); Organic Chemistry of Enzyme-Catalyzed Reactions by Richard Silverman (Academic Press, 2002); Organic Chemistry (6th Edition) by Leroy "Skip" G Wade; Organic Chemistry by T. W. Graham Solomons and, Craig Fryhle.

Material and Methods

Cells

Macrophage isolation and culture Peritoneal macrophages were collected from the peritoneal cavity of 6 to 8-weeks-old male ICR mice (Harlan, Israel) after an intraperitoneal injection of 1.5 ml of thioglycollatebroth (4%) 4 days before harvest. Peritoneal macrophages were washed three times with phosphate-buffered saline (PBS) and, when appropriate, a hypotonic lysis of erythrocytes was performed, yielding a highly enriched (90-95%) macro-phage cell population. Macrophages were identified by FACS (Becton-Dickinson, Mountain View, Calif., USA) analysis using FITC-conjugated rat anti-mouse F4/80 (MCA497F; Serotec, Oxford, UK) by flow microfluorimetry. For each sample, 10,000 light-scatter-gated viable cells were analyzed. Peritoneal macrophages ($1 \times 10^6$ cells/well) were cultured in 96-well-plates at 37° C. in a 5% $CO_2$ atmosphere in RPMI 1640 medium containing 10% fetal calf serum, 2 mM L-glutamine. 100 U/ml penicillin. 100 mg/ml streptomycin (Beit-Haemek, Israel). Cells were stimulated with 1 mg/ml LPS from *Salmonella enterica* serotype typhimurium in the absence or presence of different combination as described herein (see the figures in the examples section). The phytonutrients were dissolved in dimethylsulfoxide (DMSO; in a final concentration of 5 mM). The mixture was vortexed and incubated in a water bath at 37° C. (with shaking) for 10 mins and sonicated in a sonicator bath for 15 seconds three times. Working concentrations of the compounds were prepared from the stock solution by addition of appropriate volumes to warmed culture medium. The final concentration in solution was calculated by addition of 0.5 ml isopropanol and 1.5 ml hexane/dichloromethane (1/5 v/v) containing 0.025% BHT to 1 ml of the culture medium. The solution was vortexed and the liquid phases were separated by centrifugation at 3000 rpm for 10 min. Spectrophotometry was performed to measure the concentrations of lycopene, asthaxanthin, lutein, b-carotene. Appropriate volumes of DMSO (0.1-0.2%) were added to the controls and the percentage inhibition in each tube test was calculated in relation to its control.

Superoxide Production

1. The release of superoxide anion ($O_2^-$) was measured as the superoxide dismutase-inhibitable reduction of ferricyto-chrome c by the microtiter plate technique. The reduction of ferricytochrome c was followed by a change in absorbance at 550 nm at 2-min intervals for 30 min on a Thermomax microplate reader (Molecular Devices, Menlo Park, Calif., USA). The maximal rates of superoxide generation were determined and expressed as nmol $O_2^-/10^6$ cells/10 min using the extinction coefficient $E_{550}=21$ mM/cm.
2. The internal production of superoxide was detected by the reduction of dihydrorhodamine 123 (DHR123): $3\times10^5$ cells in 490 ml of Hanks' solution, pH=7.4, were incubated with 5 ml of DHR123 in a final concentration of 1 mM in polypropylene test tubes for 5 min at 37° C. Stimulated and unstimulated cells were immediately analyzed by FACS (BeckmanCoulter, Fullerton, Calif., USA).

Example 1

Dose Dependent Inhibition of No Production by Omega-3

The anti-inflammatory effect on cells as described herein was detected by inhibition of NO production by LPS-stimulated macrophages.

The graphs of FIGS. 1A and 1B show that combinations of omega-3 fatty acids DHA and EPA inhibited NO production in a dose dependent manner.

Example 2

Dose Dependent Synergistic Inhibition of No Production by Omega-3 and Tomato Lycopene The anti-inflammatory effect on cells as described herein was detected by inhibition of NO production by LPS-stimulated macrophages.

The graphs of FIGS. 2A-2D show that combinations of omega-3 fatty acids DHA and EPA with tomato lycopene, synergistically, inhibited NO production in certain dosages. The letter S above the horizontal lines marks a measured synergistic effect.

Example 3

Dose Dependent Synergistic Inhibition of No Production by Omega-3, Carnosic Acid, and Tomato Lycopene The anti-inflammatory effect on cells as described herein was detected by inhibition of NO production by LPS-stimulated macrophages.

The graphs of FIGS. 3A-3D and 4A-4D show that combinations of omega-3 fatty acids DHA and EPA with carnosic acid and tomato lycopene, synergistically, inhibited NO production in certain dosages. The letter S above the horizontal lines marks a measured synergistic effect.

Example 4

Dose Dependent Synergistic Inhibition of No Production by Omega-3, Carnosic Acid and Lutein The anti-inflammatory effect on cells as described herein was detected by inhibition of NO production by LPS-stimulated macrophages.

The graphs of FIGS. 5A-5D show that combinations of omega-3 fatty acids DHA and EPA with carnosic acid and lutein, synergistically, inhibited NO production in certain dosages. The letter S above the horizontal lines marks a measured synergistic effect.

Example 5

Dose Dependent Synergistic Inhibition of No Production by Omega-3, Carnosic Acid, Lutein, and Tomato Lycopene The anti-inflammatory effect on cells as described herein was detected by inhibition of NO production by LPS-stimulated macrophages.

The graphs of FIGS. 6A-6B show that combinations of omega-3 fatty acids DHA and EPA with carnosic acid, lutein and tomato lycopene, synergistically, inhibited NO production in certain dosages.

Example 6

Dose Dependent Synergistic Inhibition of No Production by Another Omega-3 Oil Alone or in Combination with Tomato Lycopene The anti-inflammatory effect on cells as described herein was detected by inhibition of NO production by LPS-stimulated macrophages.

The graphs of FIG. 7 show that another omega-3 oil with higher DHA content than EPA was also effective in the inhibition of NO production in cells (FIG. 7A). Experiments with combinations of omega-3 with higher DHA content than EPA and tomato lycopene, synergistically, inhibited NO production in cells in certain dosages as indicated.

In conclusion, the data presented herein provides highly synergistic composition having utility in anti-inflammatory applications. Furthermore, this data shows that both compositions of carnosic acid, and tomato lycopene comprising Omega-3 with high DHA and low EPA and Omega-3 with low DHA and high EPA show a synergistic effect on the anti-inflammatory NO release in cells.

The invention claimed is:

1. A composition comprising an omega-3 fatty acid and tomato lycopene, wherein the molar concentration ratio of an omega-3 fatty acid to tomato lycopene is from 2000:1 to 10:1.
2. The composition of claim 1, wherein said composition further comprises phytoene, phytofluene, beta-carotene, a tocopherol, phytosterols, or any combination thereof.
3. The composition of claim 1, further comprising lutein.
4. The composition of claim 1, wherein said composition is an oral composition.
5. The composition of claim 1, further comprising a pharmaceutical acceptable excipient.

6. The composition of claim 1, wherein said omega-3 fatty acid is docosahexaenoic acid, eicosapentaenoic acid, or a combination thereof.

\* \* \* \* \*